(12) United States Patent
Cho et al.

(10) Patent No.: US 8,084,647 B2
(45) Date of Patent: Dec. 27, 2011

(54) TWO-PHOTON PROBE FOR REAL-TIME MONITORING OF INTRACELLULAR CALCIUM IONS, METHOD FOR PREPARING THE PROBE AND METHOD FOR REAL-TIME MONITORING OF INTRACELLULAR CALCIUM IONS USING THE PROBE

(75) Inventors: Bong-Rae Cho, Seoul (KR); Hwan Myung Kim, Suwon (KR)

(73) Assignee: Korea University Industry and Academy Cooperation Foundation, Seoul (KR)

( * ) Notice: Subject to any disclaimer, the term of this patent is extended or adjusted under 35 U.S.C. 154(b) by 630 days.

(21) Appl. No.: 11/997,520

(22) PCT Filed: Jan. 21, 2008

(86) PCT No.: PCT/KR2008/000352
§ 371 (c)(1),
(2), (4) Date: May 1, 2008

(87) PCT Pub. No.: WO2009/031734
PCT Pub. Date: Mar. 12, 2009

(65) Prior Publication Data
US 2010/0105097 A1    Apr. 29, 2010

(30) Foreign Application Priority Data
Sep. 7, 2007   (KR) .................. 10-2007-0090726

(51) Int. Cl.
*C07C 211/00* (2006.01)
*A61B 5/00* (2006.01)
*A61B 8/00* (2006.01)
*A61B 10/00* (2006.01)

(52) U.S. Cl. ........................ 564/428; 424/9.6

(58) Field of Classification Search .................. None
See application file for complete search history.

(56) References Cited

OTHER PUBLICATIONS

Cho et al. Angew. Chem. Int. Ed. 2007, 46, 7445-7448.*
http://onlinelibrary.wiley.com/doi/10.1002/anie.v46:39/issuetoc#jumpTo, 2007 journal contents, p. 9.*
Derwent abstract of: American Chemical Society Conference and Meeting Abstract, 63rd Southwest Regional Meeting of the American Chemical Society, Lubbock, TX, United States, Nov. 4-7, 2007, p. 1.*

(Continued)

*Primary Examiner* — Daniel Sullivan
*Assistant Examiner* — Clinton Brooks
(74) *Attorney, Agent, or Firm* — Alston and Bird, LLP

(57) ABSTRACT

A two-photon probe for real-time monitoring of intracellular calcium ions is provided. The two-photon probe is very suitable for real-time imaging of intracellular calcium ions, shows 20~50-fold TPEF enhancement in response to $Ca^{2+}$, has a dissociation constant ($K_d^{TP}$) of 0.14±0.02 to 0.25±0.03 μM, and emits 5-fold stronger TPEF than currently available one-photon fluorescent $Ca^{2+}$ probes. Unlike the previously available probes, the two-photon probe can selectively detect dynamic levels of intracellular free $Ca^{2+}$ in live cells and living tissues without interference from other metal ions and from the membrane-bound probes. Moreover, the two-photon probe is capable of monitoring the calcium waves at a depth of 100-300 μm in live tissues for 1,100-4,000 s using two-photon microscopy (TPM) with no artifacts of photo-bleaching. Further provided are a method for preparing the two-photon probe and a method for real-time monitoring of intracellular calcium ions using the two-photon probe.

7 Claims, 14 Drawing Sheets

OTHER PUBLICATIONS

Demas et al., "The Measurement of Photoluminescence Quantum Yields," *The Journal of Physical Chemistry*, 1971, pp. 991-1024, vol. 75, No. 8.

Hirose, "A Practical Guide for the Determination of Binding Constants," *Journal of the Inclusion Phenomena and Macrocyclic Chemistry*, 2001, pp. 193-209, vol. 39.

Kim et al., "Environment-Sensitive Two-Photon Probe for Intracellular Free Magnesium Ions in Live Tissue," *Angew. Chem. Inc. Ed.*, 2007, pp. 3460-3463, vol. 46.

Koh et al., "The Role of Zinc in Selective Neuronal Death After Transient Global 1Cerebral Ischemia," *Science*, 1996, pp. 1013-1016, vol. 272.

Lee et al., "2,6-Bis[4-(p-dihexylaminostyryl)-styryl]anthracene Derivatives with Large Two-Photon Cross Sections," *American Chemical Society*, 2005, pp. 323-326, vol. 7, No. 2.

Long et al., "The Rigorous Evalation of Spectrophotometric Data to Obtain an Equilibrium Constant," *Interpretive Experiments*, 1982, pp. 1037-1039, vol. 59, No. 12.

Parri et al., "Spontaneous Astrocytic $Ca^{2+}$ Oscillations in situ Drive NMDAR-Mediated Neuronal Excitation," *Nature Neurocience*, 2001, pp. 803-812, vol. 4, No. 8.

Pethig et al., "On the Dissociation Constants of BAPTA-Type Calcium Buffers," *Cell Calcium*, 1989, pp. 491-498, vol. 10.

Grynkiewicz et al., "A New Generation of $Ca^{2+}$ Indicators With Greatly Improved Fluorescence Properties," *The Journal of Biological Chemistry*, 1985, pp. 3440-3450, vol. 260, No. 6.

Matias et al., "Effect of the Zinc Chelator N,N,N',N'-tetrakis (2-Pyridylmethyl)ethylenediamine (TPEN) on Hippocampal Mossy Fiber Calcium Signals and on Synaptic Transmission," *Biol Res*, 2006, pp. 521-530, vol. 39.

Minta et al., "Fluorescent Indicators for Cytosolic Calcium Based on Rhodamine and Fluorescein Chromophores," *The Journal of Biological Chemistry*, 1989, pp. 8171-8178, vol. 264, No. 14.

Rudolf et al., "Looking Forward to Seeing Calcium," *Nature Reviews/Molecular Cell Biology*, 2003, pp. 579-586, vol. 4.

Tsien, "New Calcium Indicators and Buffers with High Selectivity Against Magnesium and Protons: Design, Synthesis, and Properties of Prototype Structures," *Biochemistry*, 1980, pp. 2396-2404, vol. 19, No. 11.

Kim, et al. *American Chemical Society Conference and Meeting Abstract* "Two Photon Probes for Bioimaging"; Abstracts, 63rd Southwest Regional Meeting of the American Chemical Society, Lubbock, TX, United States, Nov. 4-7, 2007, GEN-073.

Cho, *American Chemical Society Conference and Meeting Presentation*, "30 Years in Physical Organic Chemistry—From TTY to KU", 63rd Southwest Regional Meeting of the American Chemical Society, Lubbock, TX, United States, Nov. 4-7, 2007.

\* cited by examiner

[Figure 1]
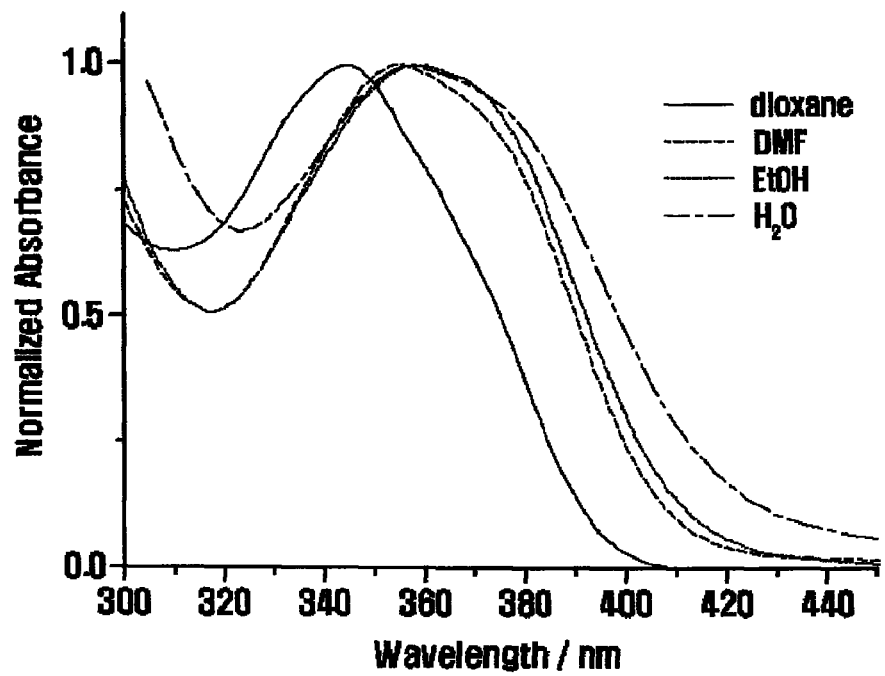
(a)
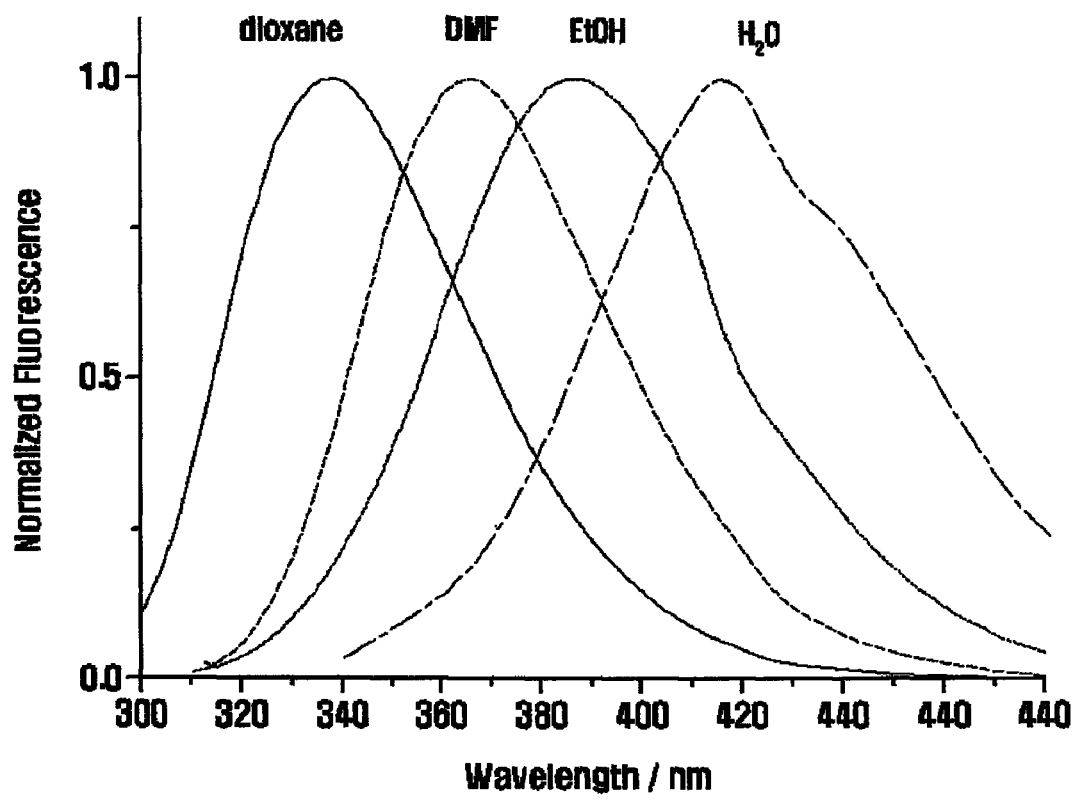
(b)

[Figure 2]
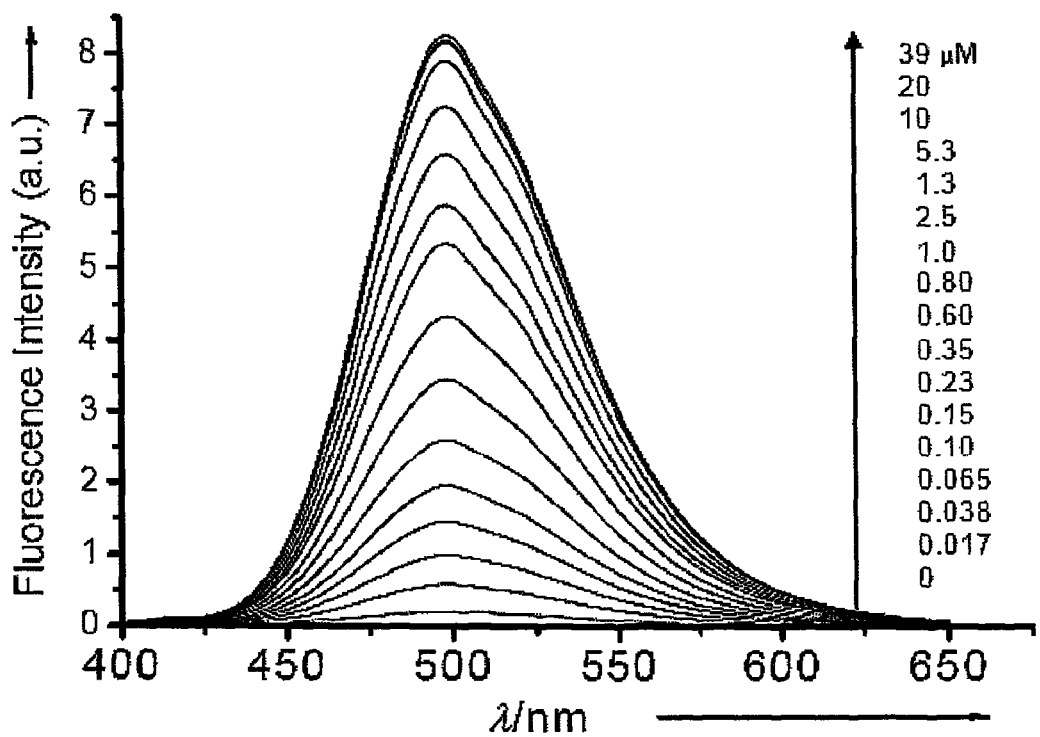
(a)
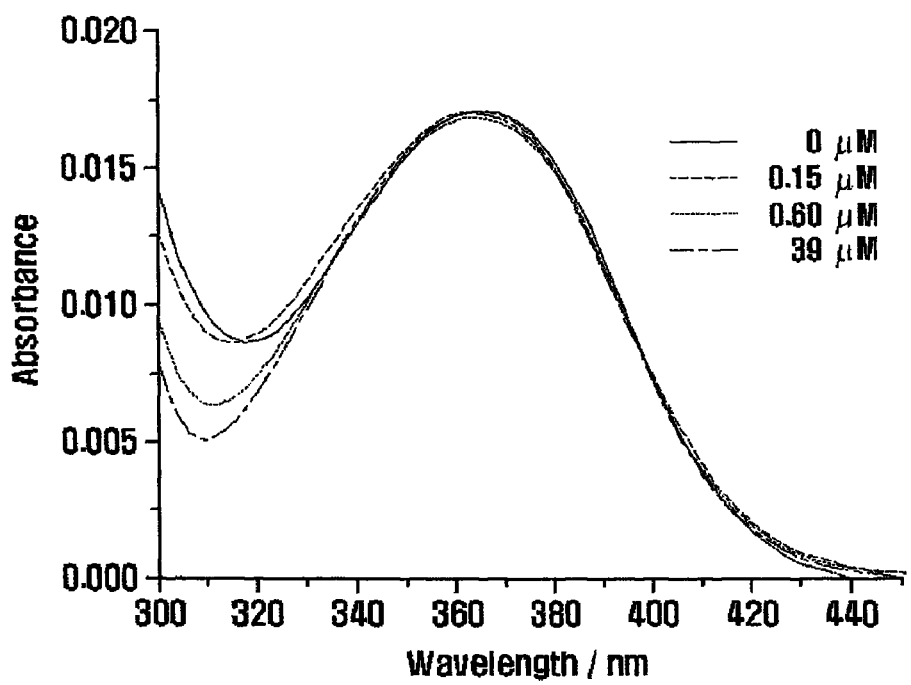
(b)

[Figure 3]
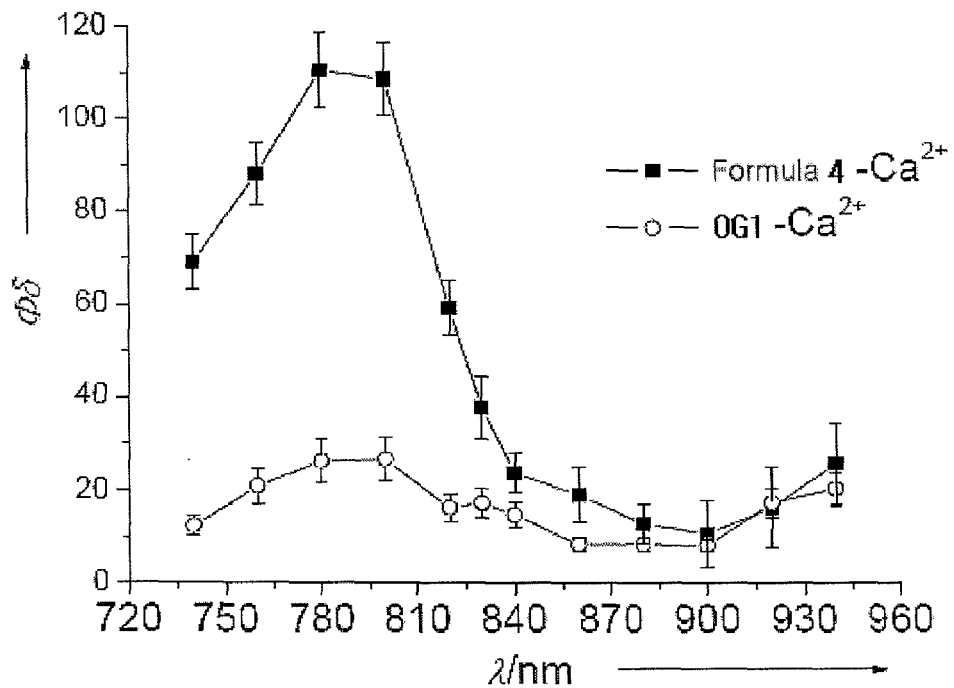
[Figure 4]
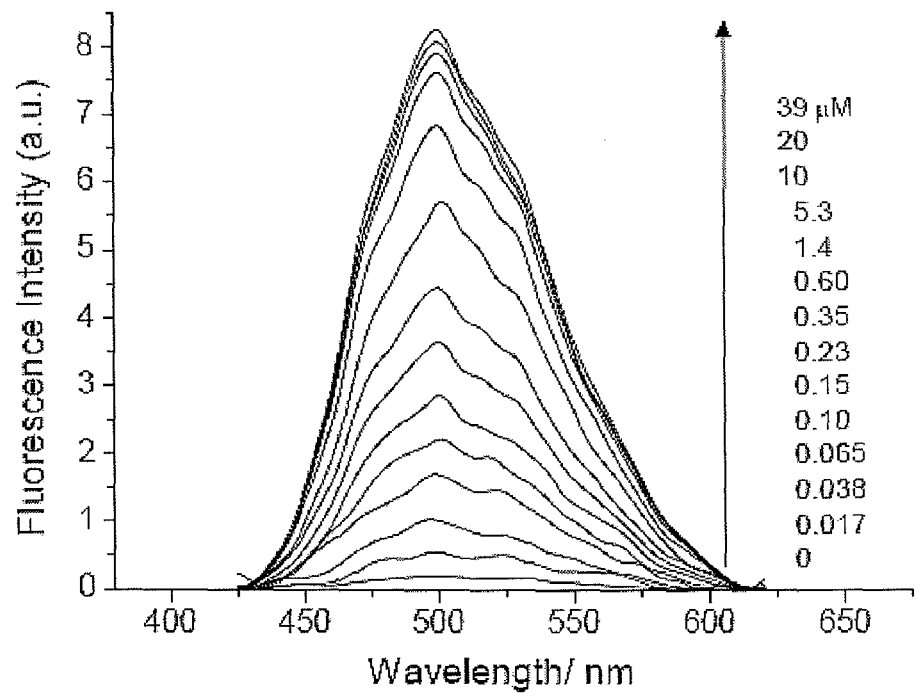

[Figure 5]
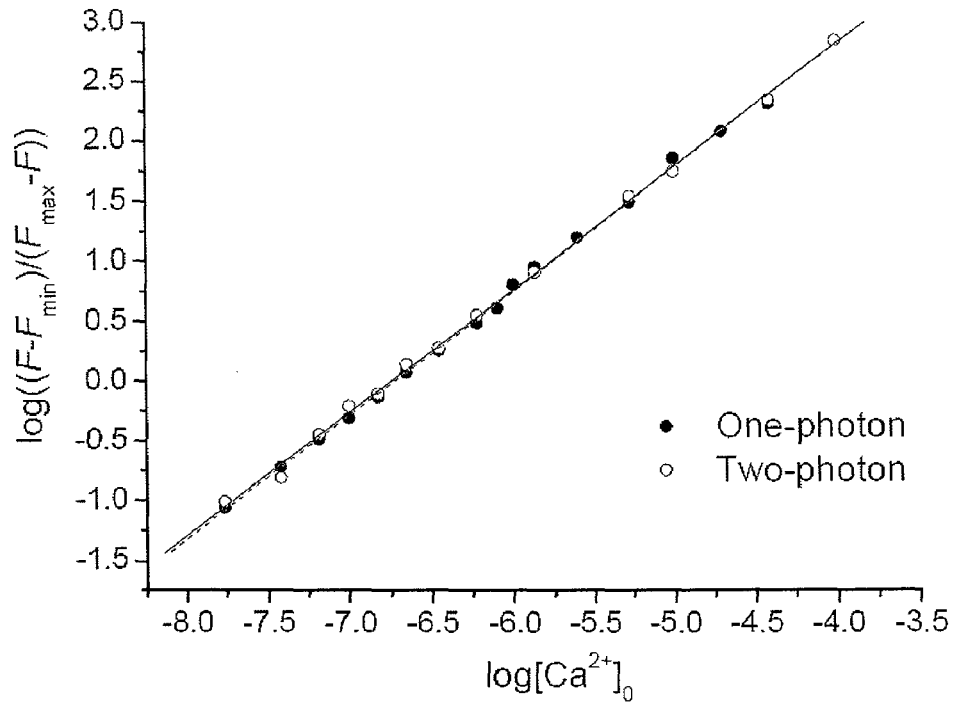
[Figure 6]
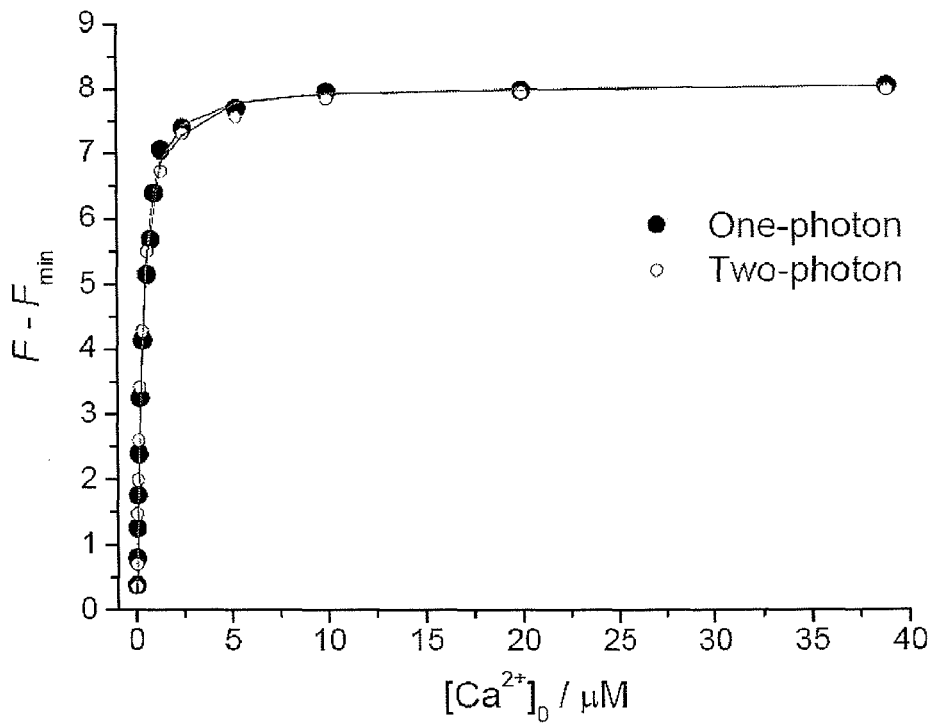

[Figure 7]
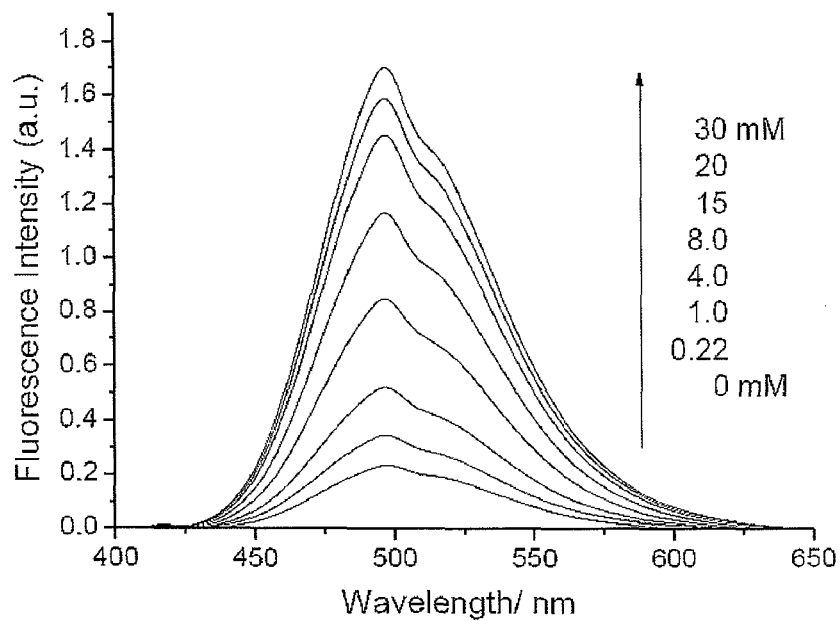
[Figure 8]
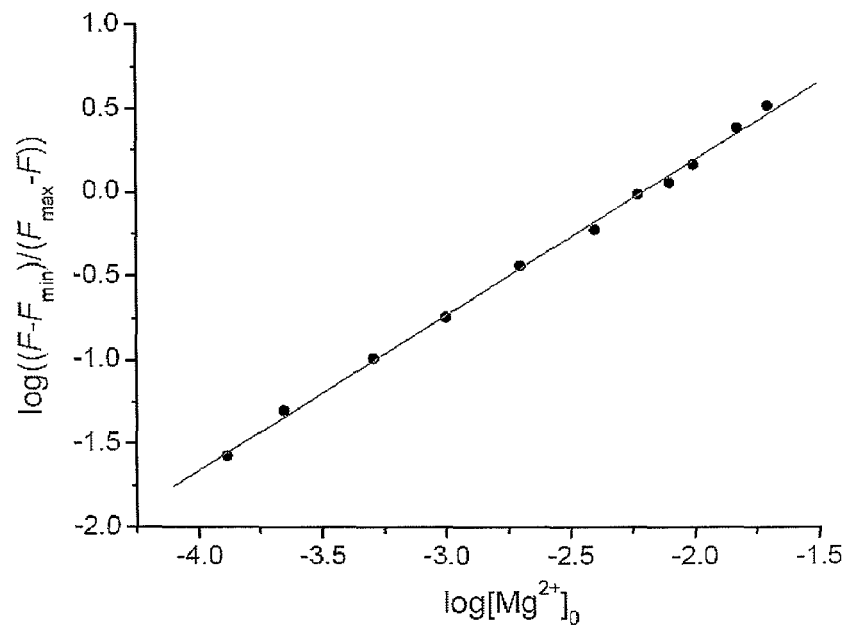

[Figure 9]
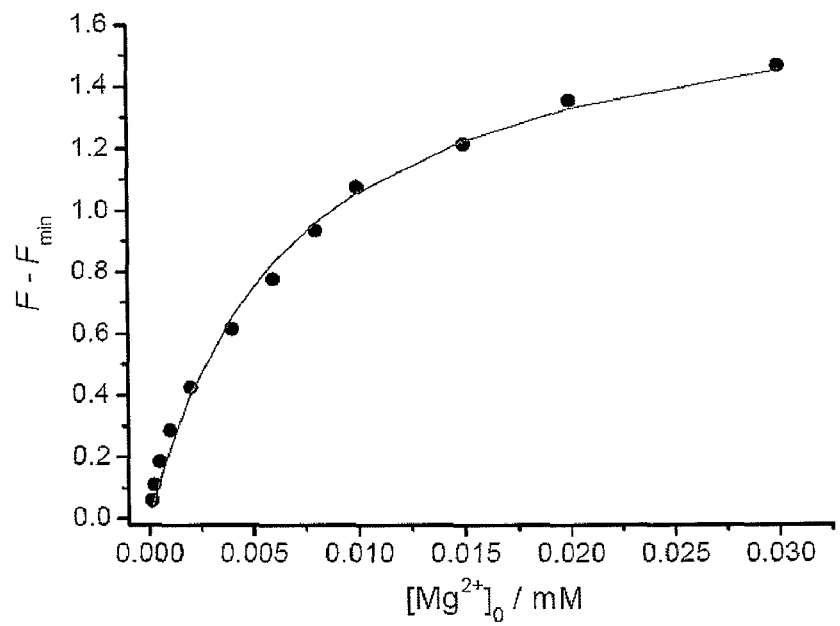
[Figure 10]
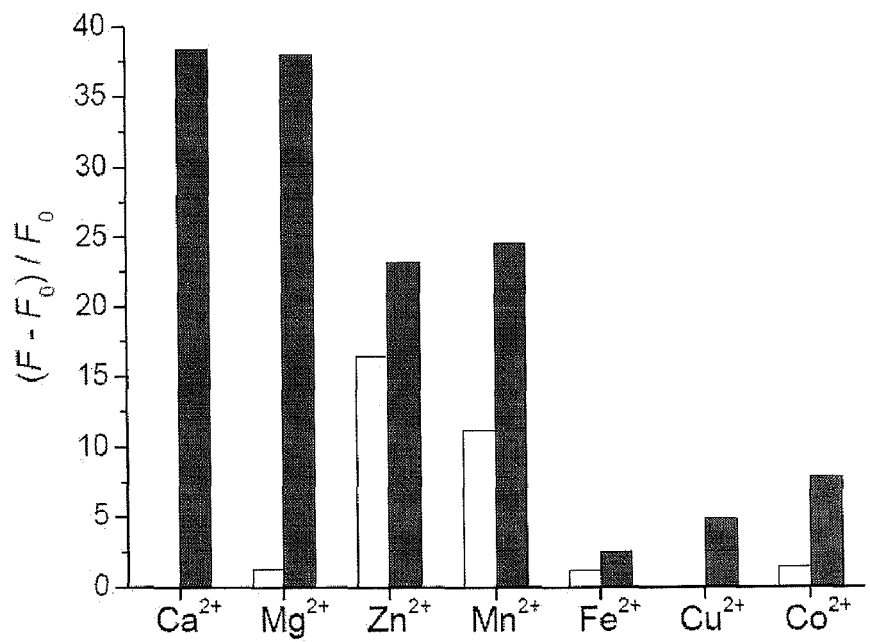

【Figure 11】
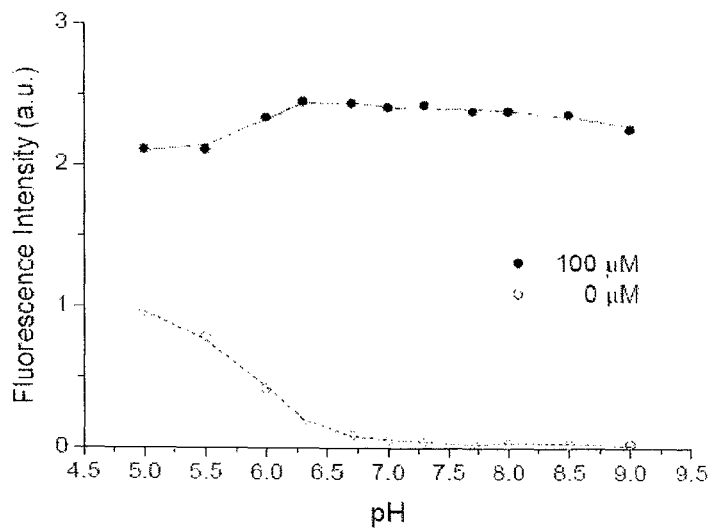
【Figure 12】
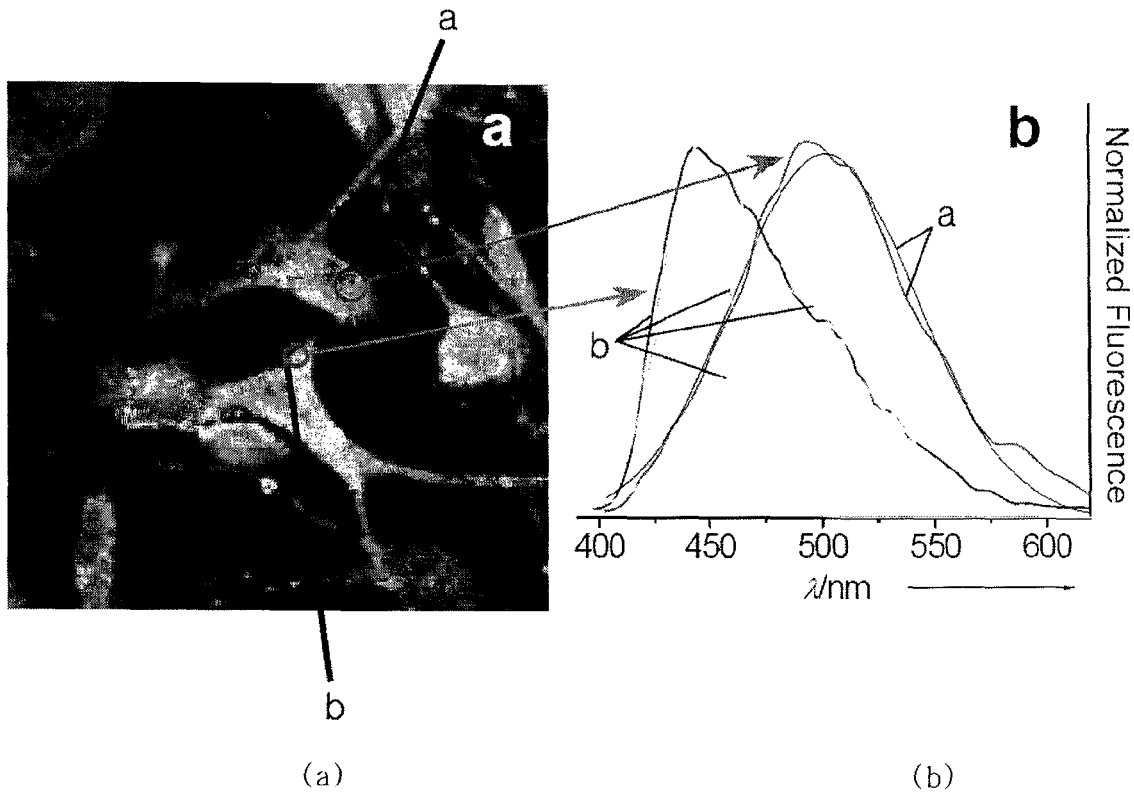
(a)  (b)

[Figure 13]
(a)
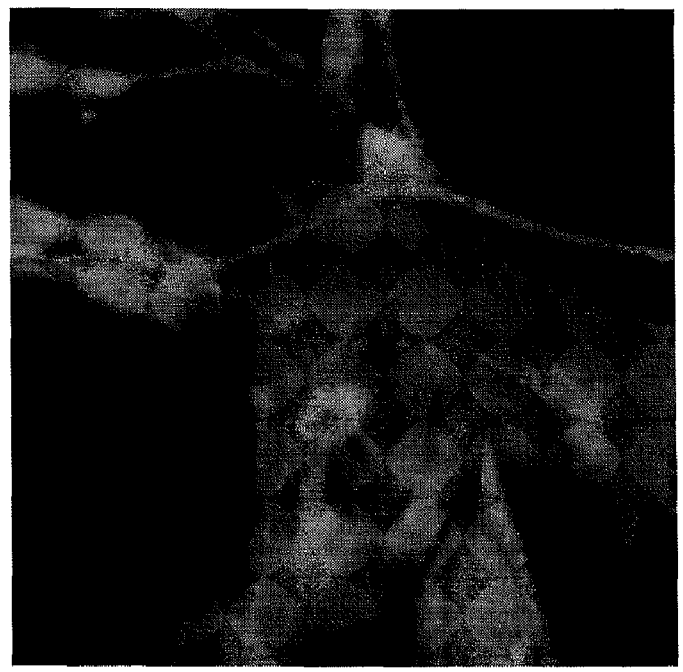
(b)

Figure 13 (continued)
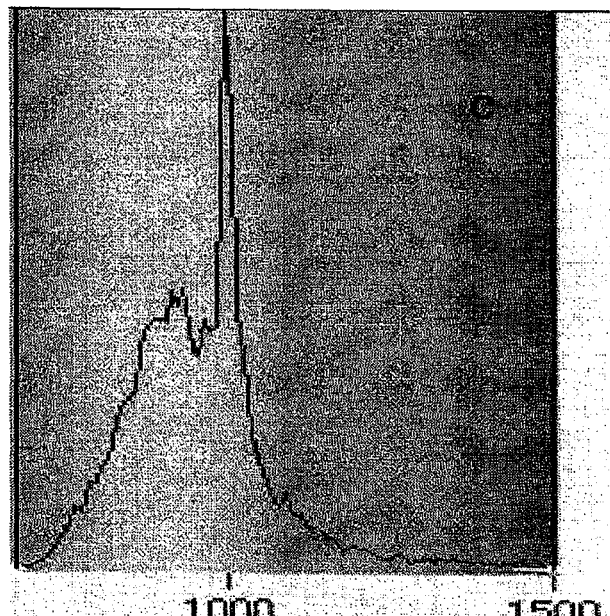
(c)
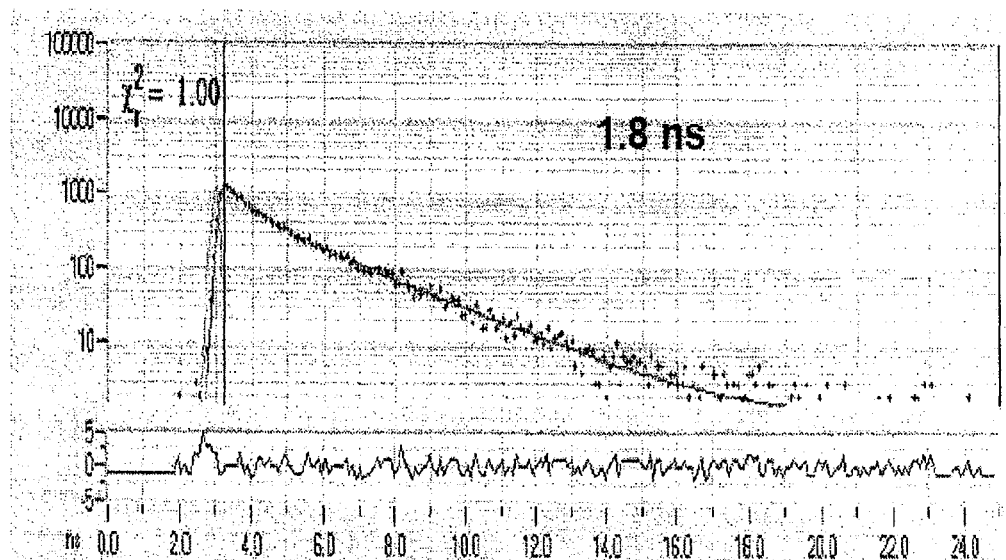
(d)

[Figure 14]
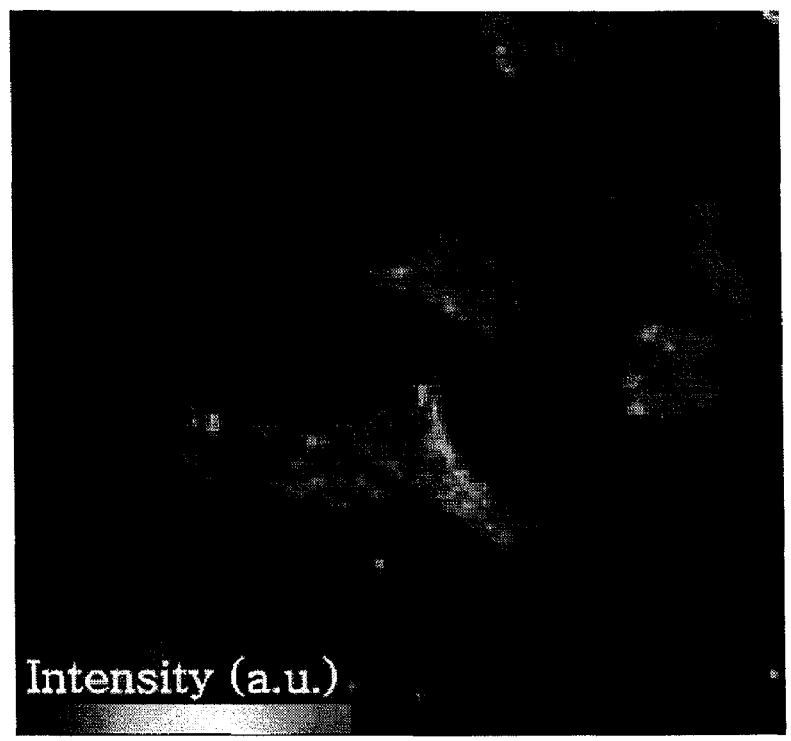
(a)
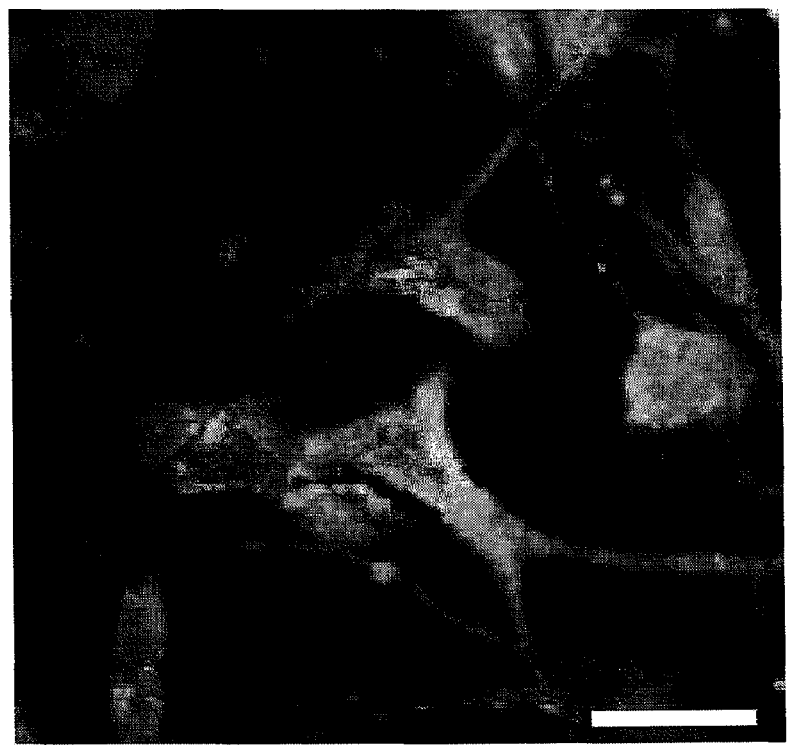
(b)

[Figure 15]
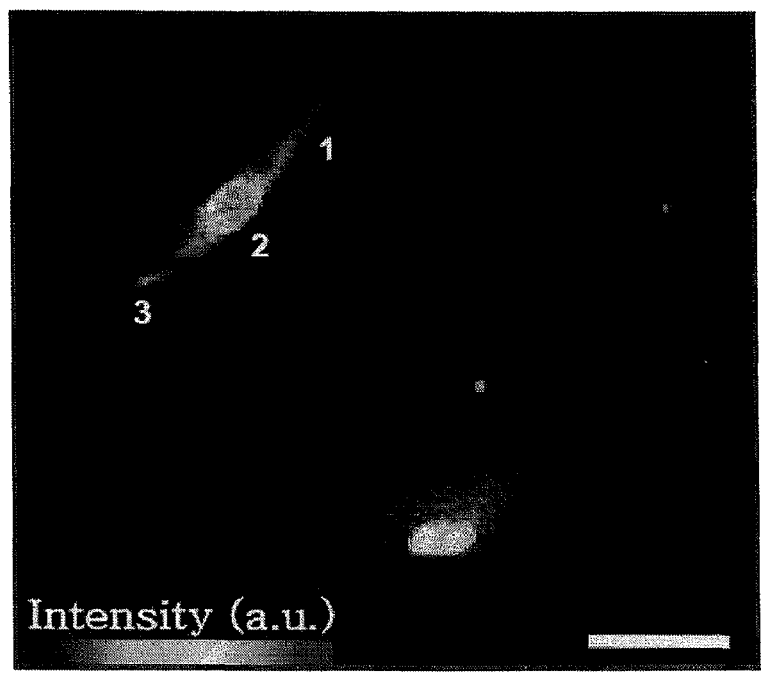
(a)
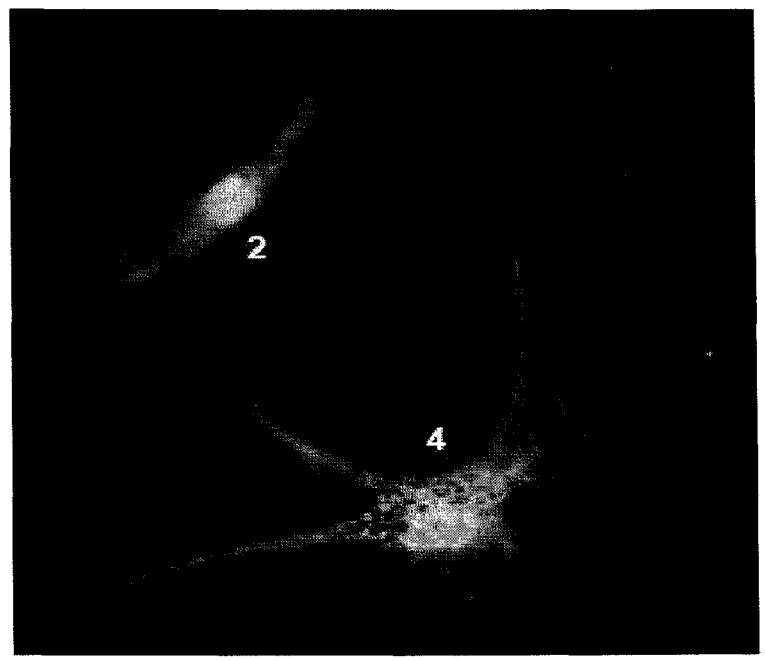
(b)

Figure 15 (continued)
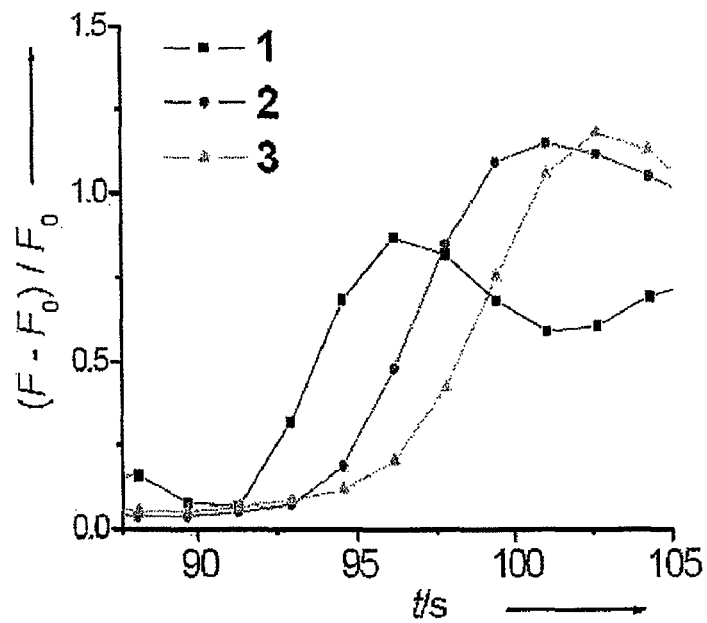
(c)
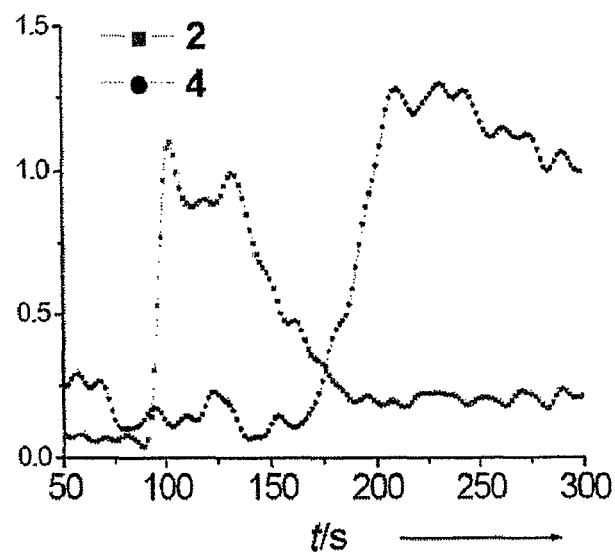
(d)

[Figure 16]
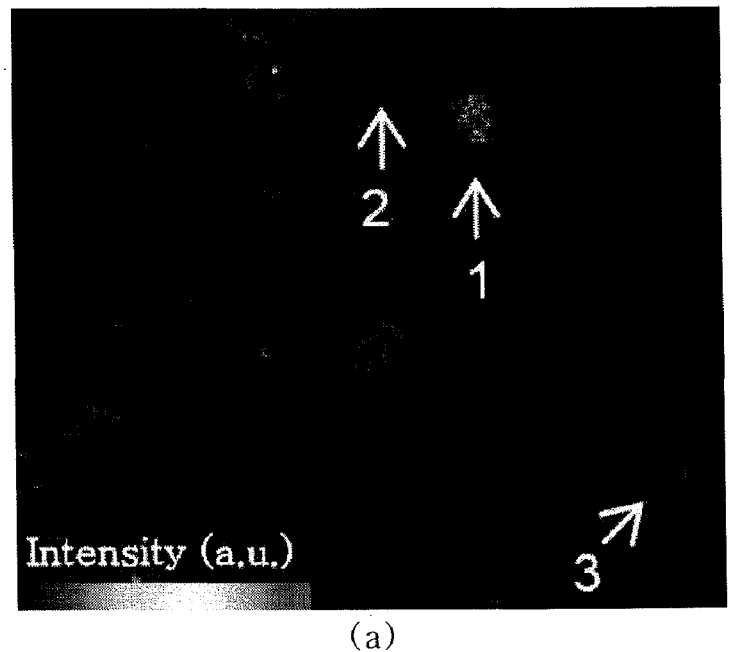
(a)
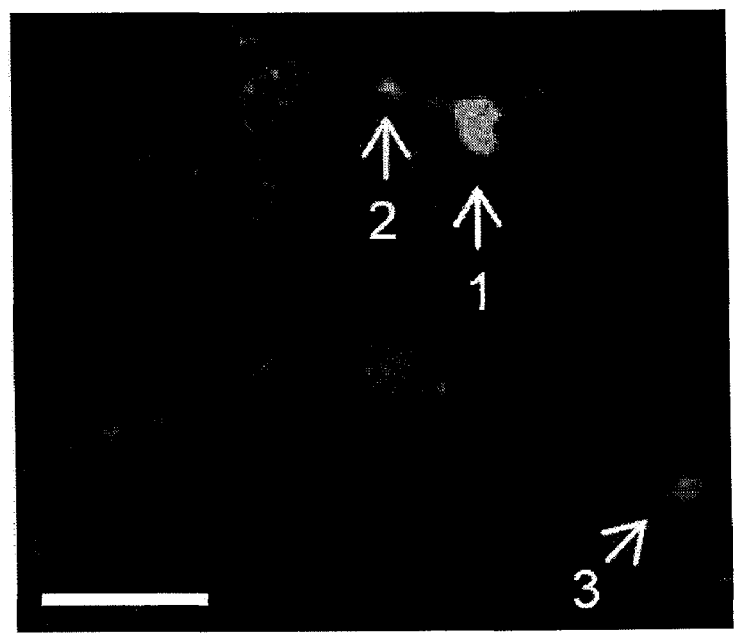
(b)

[Figure 17]
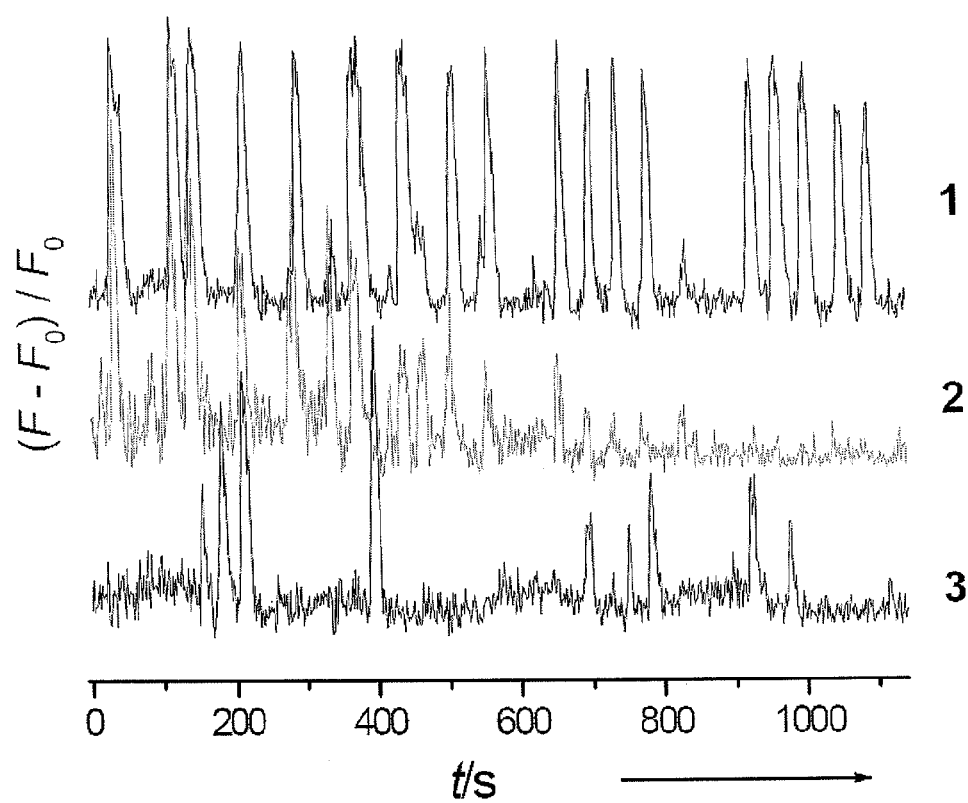

TWO-PHOTON PROBE FOR REAL-TIME MONITORING OF INTRACELLULAR CALCIUM IONS, METHOD FOR PREPARING THE PROBE AND METHOD FOR REAL-TIME MONITORING OF INTRACELLULAR CALCIUM IONS USING THE PROBE

FIELD OF THE INVENTION

The present invention relates to a two-photon probe for real-time monitoring of intracellular calcium ions, a method for preparing the two-photon probe, and a method for real-time monitoring of intracellular calcium ions using the two-photon probe. More particularly, the present invention relates to a two-photon probe suitable for real-time imaging of intracellular calcium ions due to its high two-photon absorption efficiency, ability to selectively recognize the membrane and calcium ions and high photostability, a method for preparing the two-photon probe, and a method for real-time monitoring of intracellular calcium ions using the two-photon probe.

BACKGROUND OF THE INVENTION

Calcium is a versatile intracellular signal messenger controlling numerous cellular functions. The $Ca^{2+}$-signalling system operates in many different ways to regulate various cellular processes that function over a wide dynamic range. Calcium triggers exocytosis within microseconds and drives the gene transcription and proliferation in minutes to hours.

To understand these functions, fluorescence imaging with fluorescent probes such as Oregon Green 488 BAPTA-1 (OG1) and fura-2 have most often been used. However, use of these probes with one-photon microscopy requires excitation with short wavelength light (~350-500 nm) that limits their application in tissue imaging owing to shallow penetration depth (<100 μm), photobleaching, photodamage, and cellular auto fluorescence.

Two-photon microscopy (TPM) overcomes these shortcomings. One-photon microscopy (OPM) employs one high-energy photon for excitation, whereas TPM employs two lower energy, near-infrared photons to produce an excited fluorescent substance. TPM has the advantages of localized excitation, increased penetration depth (>500 μm), lower cellular autofluorescence and self-absorption, as well as reduced photodamage and photobleaching, when compared to OPM. Thus, TPM allows imaging deep inside tissues for a long period of time without interference from artifacts of surface preparation that can extend >70 μm into the tissue slice interior.

However, most of the fluorescent probes presently used for TPM have small TP action cross sections (Φδ), demanding impractically high concentrations of probe and/or laser power. Furthermore, the fluorescence signals from membrane-bound probes can cause significant errors such as mistargeting because the fluorescence quantum yield is higher in the membrane than in the cytosol.

To the best of our knowledge, no study on two-photon dyes capable of selectively imaging calcium ions in real time has been reported. Therefore, there is a need to develop an efficient TP probe that can visualize the calcium waves deep inside the live tissue without photobleaching or mistargeting problems.

SUMMARY OF THE INVENTION

Therefore, it is a first object of the present invention to provide a two-photon (TP) probe that has the advantages of significant TP cross section for bright TPM image at low probe concentration, high selectivity for $Ca^{2+}$ ions, possible discrimination between the cytosolic and membrane-bound probes due to different emission spectra arising from the polarity of environments, and high photostability, thus being suitable for real-time imaging of intracellular calcium ions.

It is a second object of the present invention to provide a method for preparing the two-photon probe.

It is a third object of the present invention to provide a method for real-time monitoring of intracellular calcium ions using the two-photon probe.

In accordance with one aspect of the present invention, the first object can be accomplished by the provision of a two-photon probe for real-time monitoring of intracellular calcium ions, represented by Formula 1:

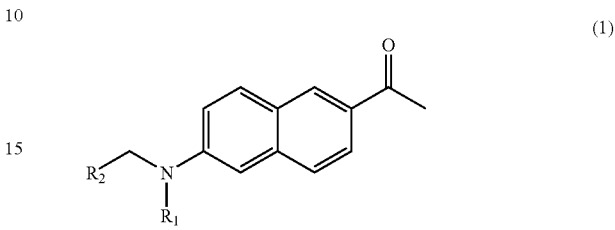

(1)

wherein $R_1$ is $CH_3$ or H, and
$R_2$ is

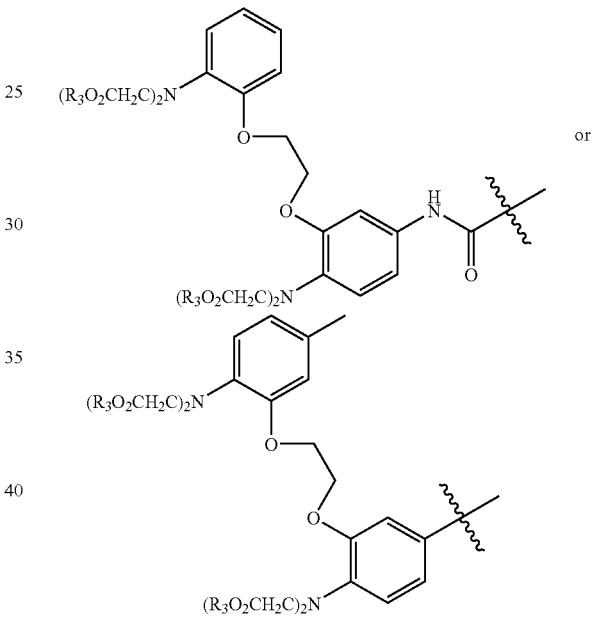

or ($R_3$=H or $CH_2OCOCH_3$).

In accordance with another aspect of the present invention, the second object can be accomplished by the provision of a method for preparing the two-photon probe for real-time monitoring of intracellular calcium ions, the method comprising reacting a compound of Formula 2:

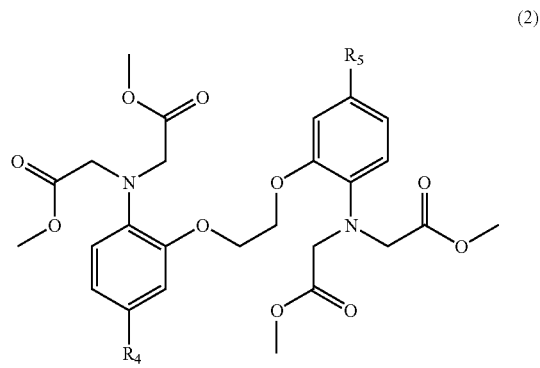

(2)

wherein $R_4$ is $NH_2$ or CHO and $R_5$ is H or $CH_3$, with a compound of Formula

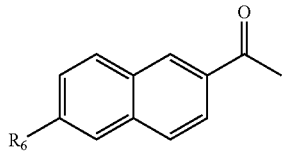 (3)

wherein $R_6$ is $NH_2$ or

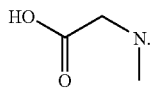

In accordance with yet another aspect of the present invention, the third object can be accomplished by the provision of a method for real-time monitoring of intracellular calcium ions, the method comprising the steps introducing the two-photon probe into cells of interest and imaging two-photon excited fluorescence emitted from the two-photon probe.

In an embodiment, the intracellular calcium ion concentration may be quantitatively determined by Equation 1:

$$[Ca^{2+}] = K_d[(F-F_{min})/(F_{max}-F)] \quad (1)$$

where $K_d$ is the dissociation constant of the two-photon probe for $Ca^{2+}$, F is the observed two-photon fluorescence intensity, $F_{min}$ is the minimum fluorescence intensity, and $F_{max}$ is the maximum fluorescence intensity.

In another embodiment, the two-photon excited fluorescence images may be collected at wavelengths ranging from 500 to 620 nm.

The two-photon probe of the present invention is suitable for real-time imaging of intracellular calcium ions because it has the advantages of significant TP cross section for bright TPM image at low probe concentration, high selectivity for $Ca^{2+}$ ions, possible discrimination between the cytosolic and membrane-bound probes due to different emission spectra with the polarity of environments (e.g., hydrophilic and hydrophobic environments), and high photostability.

The two-photon probe of the present invention uses 2-acetyl-6-(dimethylamino)naphthalene as the TP chromophore and O,O'-bis(2-aminophenyl)ethyleneglycol-N,N,N',N'-tetraacetic acid (BAPTA) as the $Ca^{2+}$ ion chelator.

The two-photon probe of the present invention shows significant TP cross section and large spectral shifts with the solvent polarity, allowing the detection of the two-photon excited fluorescence (TPEF) of the probe-$Ca^{2+}$ complex separately from that of membrane-bound probes. In addition, the two-photon probe of the present invention is capable of imaging the calcium waves in live cells and living tissue at >100 μm depth for a long period of time without mistargeting and photobleaching problems.

Considering the cell permeability of the two-photon probe according to the present invention, $R_3$ in Formula 1 is preferably $CH_2OCOCH_3$. The replacement of the hydrogen atoms with $CH_2OCOCH_3$ in $R_3$ is performed by reacting bromomethyl acetate and triethylamine with the compound of Formula 1 ($R_3$=H).

In the real-time monitoring method of the present invention, the two-photon excited fluorescence images can be collected using wavelengths between 500 nm and 620 nm and intracellular free $Ca^{2+}$ only can be selectively detected with minimum contribution from the membrane-bound two-photon probes, as will be described below.

Unlike prior art methods, the intracellular calcium ions can be quantitatively detected as well as qualitatively analyzed by the real-time monitoring method of the present invention.

The two-photon probe of the present invention is very suitable for real-time imaging of intracellular calcium ions, shows 44-fold TPEF enhancement in response to $Ca^{2+}$, has a dissociation constant ($K_d^{TP}$) of 0.25±0.03 μM, and emits 5-fold stronger TPEF than Oregon Green 488 BAPTA-1 (OG1) upon complexation with $Ca^{2+}$. Unlike the previously available probes, the two-photon probe of the present invention can selectively detect dynamic levels of intracellular free $Ca^{2+}$ in live cells and living tissues without interference from other metal ions and from the membrane-bound probes. Moreover, the two-photon probe of the present invention is capable of monitoring the calcium waves at a depth of 100-300 μm in live tissues for longer than 1,100 s using TPM with no artifacts of photo-bleaching.

BRIEF DESCRIPTION OF THE DRAWINGS

FIG. 1 shows absorption (1a) and emission (1b) spectra of the compound of Formula 7 in 1,4-dioxane, DMF, ethanol and $H_2O$;

FIG. 2 shows one-photon emission (2a) and absorption (2b) spectra of the compound of Formula 4 in the presence of free $Ca^{2+}$ at various concentrations;

FIG. 3 shows two-photon action spectra of the compound (●) of Formula 4 and OG1 (○) in the presence of free 39 μM $Ca^{2+}$;

FIG. 4 shows two-photon emission spectra of the compound of Formula 4 in the presence of free $Ca^{2+}$ at various concentrations;

FIG. 5 shows linear Hill plots for the complexation of the compound of Formula 4 with $Ca^{2+}$;

FIG. 6 shows titration curves of the compound of Formula 4, which were fitted to Equation 5;

FIG. 7 shows one-photon emission spectra of the compound of Formula 4 in the presence of free $Mg^{2+}$ at various concentrations;

FIG. 8 is a linear Hill plot for the complexation of the compound of Formula 4 with free $Mg^{2+}$ at various concentrations;

FIG. 9 is a one-photon fluorescence titration curve for the complexation of the compound of Formula 4 with free $Mg^{2+}$ at various concentrations;

FIG. 10 is a graph showing the reactivity of the compound of Formula 4 for various metal ions;

FIG. 11 is a graph showing the effect of pH on the reactivity of the compound of Formula 4;

FIG. 12 shows a pseudo colored TPM image (12a) of cultured astrocytes labeled with the compound of Formula 7 and two-photon excited fluorescence spectra (12b) from the hydrophobic and hydrophilic domains of the astrocytes;

FIG. 13 shows a one-photon fluorescence intensity image (13a) and a pseudocolored lifetime image (13b) of astrocytes labeled with the compound of Formula 7, the lifetime distribution (13c) of the astrocytes, and the results (13d) of single point analysis for the region indicated by the white arrow in FIG. 13a;

FIG. 14 shows pseudo colored TPM images of astrocytes labeled with the compound of Formula 7, which were collected at 360-460 nm (14a) and 500-620 nm (14b);

FIG. 15 shows pseudo colored TPM Images of astrocytes labeled with the compound of Formula 7, which were taken after 110 s (15a) and 220 s (15b), and time courses (15c and 15d) of the calcium waves in different locations of the astrocytes;

FIG. 16 shows pseudo colored TPM images of an acute rat hypothalamic slice stained with the compound of Formula 7, which were taken after 195 s (16a) and 214 s (16b); and FIG. 17 shows spontaneous $Ca^{2+}$ transients recorded in soma (1), astrocyte process (2), and neighboring cell (3).

DETAILED DESCRIPTION OF EMBODIMENTS OF THE INVENTION

Hereinafter, the present invention will be explained in more detail with reference to the following examples. However, these examples serve to provide further appreciation of the invention but are not meant in any way to restrict the scope of the invention.

EXAMPLES

Preparative Example 1

Synthesis of the Two-Photon Probe of the Present Invention

In this example, the compound of Formula 4 was synthesized by the following procedure.

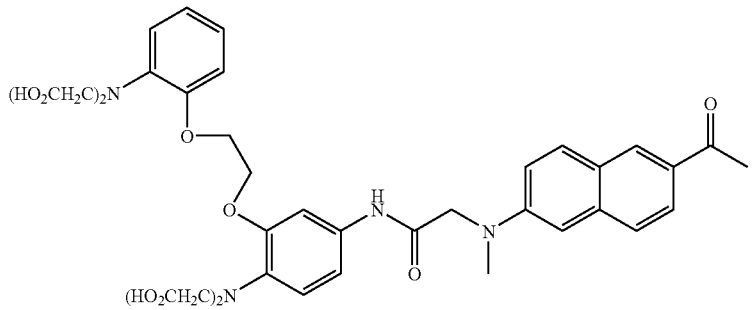

Preparative Example 1.1

Preparation of 5-nitro-BAPTA-tetramethyl ester (Formula 5) and 6-acetyl-2-[N-methyl-N-(carboxymethyl)amino]naphthalene (Formula 6)

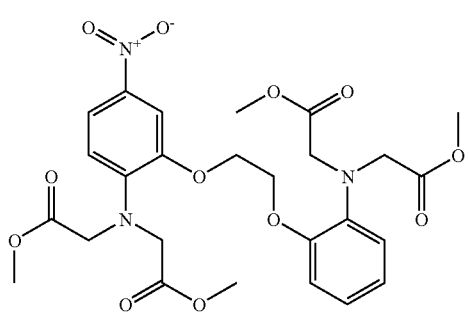

(5)

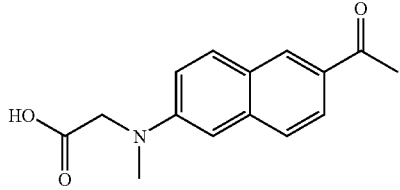

(6)

The compounds were prepared by the literature methods (R. Pethig, M. Kuhn, R. Payne, E. Adler, T.-H. Chen, L. F. Jaffe, *Cell Calcium* 1989, 10, 491-498 and H. M. Kim, C. Jung, B. R. Kim, S.-Y. Jung, J. H. Hong, Y.-G. Ko, K. J. Lee, B. R. Cho, *Angew. Chem. Int. Ed.* 2007, 46, 3460-3463).

Preparative Example 1.2

Preparation of 5-amino-BAPTA-tetramethyl ester (Formula 2)

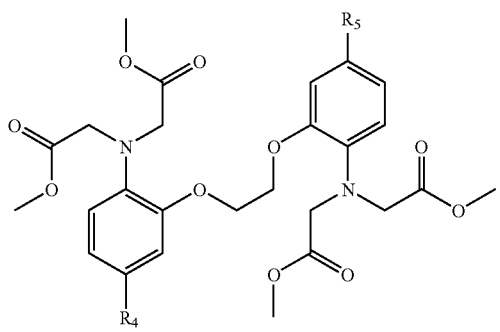

($R_4$=$NH_2$, $R_5$=H).

A mixture of the compound (2.2 g, 3.8 mmol) of Formula 5 and 5% Pd on carbon (90 mg) in ethanol was shaken under hydrogen for 5 h. The reaction mixture was filtered and washed with hot ethanol, and the solvent was removed in vacuo. The product was purified by column chromatography using ethyl acetate/hexane (2:1) as the eluent.

Yield: 1.1 g (53%); mp 121° C.; IR (KBr): 3438, 3346, 1753 cm$^{-1}$; $^1$H NMR (300 MHz, CDCl$_3$): δ 6.87 (m, 4H), 6.77 (d, 1H, J=9 Hz), 6.28 (d, 1H, J=3.0 Hz), 6.22 (dd, 1H, J=9, J=3 Hz), 4.26 (m, 4H), 4.15 (s, 4H), 4.06 (s, 4H), 3.59 (s, 6H), 3.56 (s, 6H), 3.51 (br s, 2H); $^{13}$C NMR (100 MHz, CDCl$_3$): δ=172.4, 172.3, 152.2, 150.6, 142.7, 139.4, 131.5, 122.5, 121.6, 119.2, 113.3, 113.2, 107.8, 101.8, 67.3, 67.2, 53.9, 53.5, 51.9, 51.7 ppm; Anal. Calcd for C$_{26}$H$_{33}$N$_3$O$_{10}$: C, 57.03; H, 6.07; N, 7.67. Found: C, 57.11; H, 6.05; N, 7.60.

Preparative Example 1.3

Preparation of Compound of Formula 4

A mixture of the compound (0.38 g, 1.48 mmol) of Formula 6 and 1-ethyl-3-(3-dimethylaminopropyl)-carbodiimide.HCl (0.34 g, 1.80 mmol) in DMF (5 mL) was stirred for 20 min. To this mixture, the compound (0.90 g, 1.64 mmol) of Formula 2 and 4-dimethylaminopyridine (26 mg, 0.22 mmol) were added and stirred for 12 h under N$_2$. The product was extracted with chloroform, dried over MgSO$_4$, and the solvent was removed in vacuo. The product was purified by column chromatography using hexane/ethyl acetate (2:3) as the eluent. It was further purified by recrystallization from EtOH.

Yield: 0.62 g (53%); mp 148° C.; IR (KBr): 3260, 1755, 1662 cm$^{-1}$; $^1$H NMR (400 MHz, CDCl$_3$): δ 8.35 (d, 1H, J=2 Hz), 8.18 (s, 1H), 7.98 (dd, 1H, J=9, J=2 Hz), 7.87 (d, 1H, J=9 Hz), 7.70 (d, 1H, J=9 Hz), 7.27 (d, 1H, J=2 Hz), 7.16 (dd, 1H, J=9, J=2 Hz), 7.06 (d, 1H, J=2.0 Hz), 6.88 (m, 6H), 4.25 (s, 4H), 4.12 (s, 4H), 4.10 (s, 6H), 3.56 (s, 6H), 3.53 (s, 6H), 3.24 (s, 3H), 2.68 (s, 3H); $^{13}$C NMR (100 MHz, CDCl$_3$): δ=198.0, 172.2, 172.0, 168.0, 150.8, 150.5, 149.3, 139.4, 137.3, 136.4, 132.3, 132.2, 131.6, 130.4, 127.0, 126.6, 125.2, 122.5, 121.7, 119.4, 119.2, 116.7, 113.3, 112.9, 107.7, 106.1, 77.4, 67.5, 67.1, 59.5, 53.6, 51.9, 51.8, 40.4, 26.8 ppm; Anal. Calcd for C$_{41}$H$_{46}$N$_4$O$_{12}$: C, 62.59; H, 5.89; N, 7.12. Found: C, 62.52; H, 5.93; N, 7.07.

This ester (0.50 g, 0.64 mmol) was hydrolyzed by the method as described above. The resulting precipitate was collected, washed with distilled water, and purified by crystallization from MeOHCHCl$_3$-petroleum ether.

Yield: 0.27 g (58%); mp 145° C.; IR (KBr): 3250, 2910, 1745, 1660 cm$^{-1}$; $^1$H NMR (400 MHz, CD$_3$OD): δ 8.39 (d, 1H, J=2 Hz), 7.86 (d, 1H, J=9 Hz), 7.85 (dd, 1H, J=9, J=2 Hz), 7.65 (d, 1H, J=9 Hz), 7.46 (d, 1H, J=2 Hz), 7.24 (dd, 1H, J=9, J=2 Hz), 6.96 (m, 7H), 4.31 (s, 4H), 4.30 (s, 2H), 3.91 (s, 8H), 3.24 (s, 3H), 2.63 (s, 3H); $^{13}$C NMR (100 MHz, CD$_3$OD): δ=199.2, 173.9, 173.8, 170.0, 150.6, 150.5, 149.9, 149.8, 138.7, 138.0, 137.9, 135.3, 134.2, 130.8, 130.7, 126.3, 126.2, 125.8, 124.1, 123.6, 121.3, 118.7, 118.4, 116.2, 113.0, 112.5, 105.8, 66.8, 66.5, 56.3, 54.5, 39.2, 25.3 ppm. Anal. Calcd for C$_{37}$H$_{38}$N$_4$O$_{12}$: C, 60.82; H, 5.24; N, 7.67. Found: C, 60.72; H, 5.34; N, 7.59

Preparative Example 2

Synthesis of the Two-Photon Probe of the Present Invention

In this example, the compound of Formula 7 was synthesized by the following procedure.

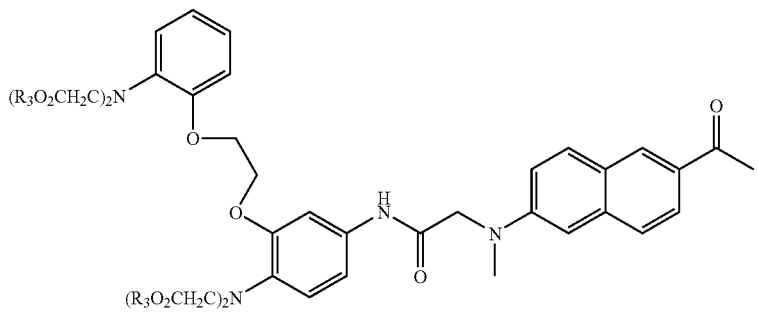

(7)

(R$_3$=CH$_2$OCOCH$_3$).

A mixture of the compound (0.11 g, 0.15 mmol) of Formula 4, bromomethyl acetate (0.24 g, 1.55 mmol), and Et$_3$N (0.14 g, 1.05 mmol) in CHCl$_3$ (5 mL) was stirred under N$_2$ for 24 h. The solution was removed in vacuo and the crude product was purified by column chromatography using ethyl acetate/hexane (3:1) as the eluent. It was further purified by recrystallization from MeOH to obtain a pale yellow solid.

Yield: 85 mg (56%); mp 137° C.; IR (KBr): 1759, 1710, 1665 cm$^{-1}$; $^1$H NMR (400 MHz, CDCl$_3$): δ 8.36 (d, 1H, J=2 Hz), 8.22 (s, 1H), 7.98 (dd, 1H, J=9, J=2 Hz), 7.88 (d, 1H, J=9 Hz), 7.71 (d, 1H, J=9 Hz), 7.31 (d, 1H, J=2 Hz), 7.17 (dd, 1H, J=9, J=2 Hz), 7.07 (d, 1H, J=2 Hz), 6.88 (m, 6H), 5.62 (s, 4H), 5.60 (s, 4H), 4.29 (s, 4H), 4.18 (s, 4H), 4.15 (s, 4H), 4.12 (s, 2H), 3.25 (s, 3H), 2.69 (s, 3H), 2.05 (s, 6H), 2.04 (s, 6H); $^{13}$C NMR (100 MHz, CDCl$_3$): δ=198.0, 170.4, 170.2, 169.7, 168.1, 151.0, 150.6, 149.3, 138.8, 137.3, 135.7, 132.9, 132.3, 131.5, 130.3, 127.0, 126.6, 125.2, 123.2, 121.9, 120.4, 120.0, 116.7, 113.8, 113.1, 107.7, 106.5, 79.5, 79.4, 77.5, 77.4, 77.1, 67.5, 67.2, 59.5, 53.5, 40.4, 26.7, 20.9 ppm; Anal. Calcd for C$_{49}$H$_{54}$N$_4$O$_{20}$: C, 57.76; H, 5.34; N, 5.50. Found: C, 57.70; H, 5.31; N, 5.52.

Example 1

Measurements of Absorption and Emission Spectra

The absorption spectra of the compound of Formula 7 were recorded on a Hewlett-Packard 8453 diode array spectrophotometer, and the fluorescence spectra of the compound were obtained with Amico-Bowman series 2 luminescence spectrometer with a 1 cm standard quartz cell. The fluorescence quantum yield of the compound was determined by using Coumarin 307 as the reference by the literature method (J. N. Demas, G. A. Crosby, *J. Phys. Chem.* 1971, 75, 991-1024.). FIG. 1 shows the absorption (1a) and emission (1b) spectra of the compound in 1,4-dioxane, DMF, ethanol and H$_2$O. The absorption and emission maxima of the compound in various solvents are shown in Table 1.

TABLE 1

| Compound | Solvent ($E_T^N$)* | $\lambda_{max}^{(l)}$ (nm) | $\lambda_{max}^{fl}$ (nm) |
|---|---|---|---|
| Formula 7 | 1,4-dioxane (0.164) | 345 | 413 |
| | DMF (0.386) | 355 | 440 |
| | Ethanol (0.654) | 359 | 473 |
| | H$_2$O (1.000) | 362 | 495 |

*The numbers in the parenthesis are normalized empirical parameter of solvent polarity (C. Reichardt, Chem Rev. 1994, 94, 2319-2358).

The absorption and emission spectra of the compound of Formula 7 showed gradual red shifts with the solvent polarity in the order 1,4-dioxane<DMF<ethanol<H$_2$O. The effect was greater for the emission (82 nm) than for the absorption spectrum (17 nm), thus indicating the utility of the compound of the Formula 7 as a polarity probe. In addition, $\lambda_{max}^{fl}$ of the compound of Formula 7 in DMF was similar to that of the membrane-bound probes (FIG. 4b), suggesting that it can be used as the model for membrane-bound probe.

FIG. 2 shows one-photon emission (2a) and absorption (2b) spectra of the compound (1 μM, 30 mM MOPS, 100 mM KCl, 10 mM EGTA, pH 7.2) of Formula 4 in the presence of free Ca$^{2+}$ at various concentrations (0-39 μM); FIG. 3 shows two-photon action spectra of the compound (●) of Formula 4 and OG1 (○) in the presence of free 39 μM Ca$^{2+}$; and FIG. 4 shows two-photon emission spectra of the compound (1 μM, 30 mM MOPS, 100 mM KCl, 10 mM EGTA, pH 7.2) of Formula 4 in the presence of free $Ca^{2+}$ at various concentrations.

When $Ca^{2+}$ was added to the compound of Formula 4 in MOPS buffer solution (30 mM, pH 7.2), the fluorescence intensity increased dramatically as a function of metal ion concentration without affecting the absorption spectra (FIG. 2), probably due to the blocking of the photo-induced electron transfer (PET) process by the complexation of metal ion.

A nearly identical result was observed in the two-photon process (FIGS. 3 and 4). The fluorescence enhancement factor [$(F-F_{min})/F_{min}$] of the compound of Formula 4 was 40 in the presence of 39 μM $Ca^{2+}$, nearly 3-fold larger than the value of 14 previously reported for OG1 (R. Rudolf, M. Mongillo, R. Rizzuto, T. Pozzan, *Nat. Rev. Mol. Cell. Biol.* 2003, 4, 579-586). Moreover, linear Hill plots determined for $Ca^{2+}$ binding with slopes of 1.0 indicated 1:1 complexation between the probe and the cations (FIG. 5) (K. A. Connors, *Binding Constants* John Wiley & Sons, Inc.: New York, 1987).

Example 2

Determination of Dissociation Constants ($K_d$)

A series of calibration solutions containing various [$Ca^{2+}$] was prepared by mixing two solutions (solution A containing 10 mM $K_2$EGTA and solution B containing 10 mM CaEGTA) in various ratios. Both solutions contained the compound (1 μM) of Formula 4, 100 mM KCl, 30 mM MOPS, and they were adjusted to pH 7.2.

To determine the $K_d$ for $Ca^{2+}$-the compound of Formula 4, the fluorescence spectrum was recorded with 2.0 mL of solution A (0 μM free $Ca^{2+}$) at 20° C. Then, 203 μl of this solution was discarded and replaced by 203 μl of solution B (39 μM free $Ca^{2+}$), and the spectrum was recorded. This brings the CaEGTA concentration to 1.00 mM and the [$Ca^{2+}$]$_{free}$ to about 0.017 μM with no change in the concentration of the probe or of the total EGTA. The [$Ca^{2+}$]$_{free}$ is calculated from the $K_d$ of EGTA for $Ca^{2+}$ (150.5 nM) using Equation 2:

$$[Ca^{2+}]_{free} = K_d^{EGTA} \times \frac{[CaEGTA]}{[K_2EGTA]} \quad (2)$$

Further, iterations attained 0.038, 0.065, 0.101, 0.150, 0.230, 0.350, 0.601, 0.800, 1.00, 1.30, 2.50, 5.30, 10.0, and 20.0 μM free $Ca^{2+}$ by successively discarding 223, 251, 285, 327, 421, 479, 667, 420, 350, 412, 905, 1028, 926, and 992 μl of solution A and replacing each with an equal volume of solution B.

When a 1:1 metal-ligand complex is formed between the compound of Formula 4 and $Ca^{2+}$, the equilibrium can be described by Equation 3:

$$[LM]^1 - ([L]_0 + [M]_0 + K_d)[LM] + [L]_0[M]_0 = 0 \quad (3)$$

where L and M represent the compound of Formula 4 and $Ca^{2+}$, respectively.

The total probe and metal ion concentration are defined as $[L]_0 = [L] + [LM]$ and $[M]_0 = [M] + [LM]$, respectively. With $[L]_0$ and $[M]_0$, the value of $K_d$ is given by:

$$[LM] = \frac{([L]_0 + [M]_0 + K_d) - \sqrt{([L]_0 + [M]_0 + K_d)^2 - 4[L]_0[M]_0}}{2}; \quad (4)$$

$$(F - F_{min}) = \left(\frac{([L]_0 + [M]_0 + K_d) - \sqrt{([L]_0 + [M]_0 + K_d)^2 - 4[L]_0[M]_0}}{2[L]_0}\right)(F_{max} - F_{min}) \quad (5)$$

where F is the observed fluorescence intensity, $F_{min}$ is the minimum fluorescence intensity, and $F_{max}$ is the maximum fluorescence intensity. The $K_d$ value that best fits the titration curve (FIG. 6) with Equation 5 was calculated by using the Excel program as reported (J. R. Long, R. S. Drago, *J. Chem. Ed.* 1982, 59, 1037; K. Hirose, *J. Incl. Phenom. Macrocycl. Chem.* 2001, 39, 193).

In order to determine the $K_d^{TP}$ for the two-photon process, the TPEF spectra were obtained with a DM IRE2 Microscope (Leica) excited by a mode-locked titanium-sapphire laser source (Coherent Chameleon, 90 MHz, 200 fs) set at wavelength 780 nm and output power 1230 mW, which corresponded to approximately 10 mW average power in the focal plane. The TPEF titration curves (FIG. 6) were obtained and fitted to Equation 3.

The dissociation constants ($K_d^{OP}$) were calculated from the fluorescence titration curves (FIG. 6), as reported (J. R. Long, R. S. Drago, *J. Chem. Educ.* 1982, 59, 1037-1039).

One-photon emission spectra of the compound of Formula 4 (30 mM MOPS, 100 mM KCl, 10 mM EGTA, pH 7.2) in the presence of free $Mg^{2+}$ (0-30 mM), a Hill plot for the complexation of the compound of Formula 4 with free $Mg^{2+}$ (0-30 mM), and a one-photon fluorescence titration curve for the complexation of the compound of Formula 4 with free $Mg^{2+}$ (0-30 mM) were obtained and are shown in FIGS. 7, 8 and 9, respectively.

The $K_d^{OP}$ values of the compound of Formula 4 for $Ca^{2+}$ and $Mg^{2+}$ were 0.27±0.01 μM and 6.8±0.7 mM, respectively. A similar value was determined in the two-photon process [$K_d^{TP}(Ca^{2+})$=0.25±0.03 μM]. The compound of Formula 4 showed modest response toward $Zn^{2+}$ and $Mn^{2+}$, much weaker response toward $Mg^{2+}$, $Fe^{2+}$ and $CO^{2+}$, and no response toward $Cu^{2+}$ (FIG. 10).

Because the intracellular concentrations of free $Mn^{2+}$ is negligible and chelatable $Zn^{2+}$ is essentially nonexistent except in specialized areas such as the hippocampal CA3 region, the probe of the present invention can selectively detect the intracellular $Ca^{2+}$ concentration ([$Ca^{2+}$]$_i$) without interference from other metal ions. Furthermore, the compound of Formula 4 is pH-insensitive in the biologically relevant pH range (FIG. 11).

Example 3

Observations of Two-Photon Action Spectra

The TP action spectra of the $Ca^{2+}$ complexes with the compound of Formula 4 and OG1 in buffer solutions indicated a value of 110 GM at 780 nm for Φδ for the compound of Formula 4-$Ca^{2+}$, 5-fold larger than that of OG1-$Ca^{2+}$. Thus, TPM images for samples stained with the compound of Formula 4 would be much brighter than those stained with commercial probe. In addition, the two-photon fluorescence enhancement factor (TFEF) estimated from the two-photon titration curve was 44 (Table 2), a value that allowed detection of $Ca^{2+}$ by TPM.

TABLE 2

| compd[a] | $\lambda_{max}^{(1)[b]}$ | $\lambda_{max}^{fl[b]}$ | $\Phi^{[c]}$ | $K_d^{OP}/K_d^{TP[d]}$ | $FEF^{OP}/FEF^{TP[e]}$ | $\lambda_{max}^{(2)[f]}$ | $\delta^{[g]}$ | $\Phi\delta^{[h]}$ |
|---|---|---|---|---|---|---|---|---|
| ACa1-AM | 362 | 495 | 0.060[i] | | | nd[j] | nd[j] | nd[j] |
| ACa1 | 365 | 498 | 0.012 | | | nd[j] | nd[j] | nd[j] |
| ACa1 + Ca$^{2+}$ | 365 | 498 | 0.49 | 0.27[k]/0.25 | 40/44 | 780 | 230 | 110 |
| OG1 + Ca$^{2+}$ | 494 | 523 | 0.66 | 0.17[l]/nd | 14[l]/nd | 800 | 37 | 24 |

[a]All data were measured in 30 mM MOPS, 100 mM KCl, 10 mM EGTA, pH 7.2 in the absence and presence (39 μM) of free Ca$^{2+}$.
[b]$\lambda_{max}$ of the one-photon absorption and emission spectra in nm.
[c]Fluorescence quantum yield, ±10%.
[d]Dissociation constants for Ca$^{2+}$ in μM measured by one- ($K_d^{OP}$) and two-photon ($K_d^{TP}$) processes, ±12%.
[e]Fluorescence enhancement factor, (F − $F_{min}$)/$F_{min}$ measured by one-(FEFOP) and two-photon (FEFTP) processes.
[f]$\lambda_{max}$ of the two-photon excitation spectra in nm.
[g]The peak two-photon cross section in 10$^{-50}$ cm$^4$s/photon (GM), ±15%.
[h]Two-photon action cross section.
[i]$\Phi$ = 0.27 ± 0.02 (compound of Formula 4) and 0.22 ± 0.02 (compound of Formula 7) in DMF.
[j]The two-photon excited fluorescence intensity was too weak to measure the cross section accurately.
[k]$K_d^{OP}$ value of the compound of Formula 4 for Mg$^{2+}$ was 6.8 ± 0.7 mM.
[l]A Guide to Fluorescent Probes and Labeling Technologies, 10th ed., (Ed.: R. R Haugland), Molecular Probes, Eugene, OR, 2005.

The two-photon cross section ($\delta$) was determined by using femto second (fs) fluorescence measurement technique (S. K. Lee, W. J. Yang, J. J. Choi, C. H. Kim, S.-J, Jeon, B. R. Cho, *Org. Lett.* 2005, 7, 323-326).

Example 4

Observation of Cells Using the Two-Photon Probe of the Present Invention

Astrocytes were taken from cerebral cortices of 1-day-old rats (Sprague-Dawley; SD). Cerebral cortices were dissociated in Hank's balanced salt solution (HBSS; Gibco BRL, Gaithersburg, Md., USA) containing 3 U/ml papain (Worthington Biochemical Corporation, NJ, USA) and plated in 75 mm flasks. To prepare purified astrocytes culture, flasks were shaken for 6 h on a shaker at 37° C., and the floating cells that were displaced into the media were removed. Astrocytes were passaged with 5 min exposure to 0.25% trypsin and replated onto poly-D-lysin-coated glass coverslips at 50~100 cells/mm$^2$ and were maintained in Dulbecco's modified Eagle's medium (DMEM; Gibco) supplemented with penicillin/streptomycin and 10% fetal bovine serum (FBS; Gibco) in a CO$_2$ incubator at 37° C. After 7-15 days in vitro, astrocytes were washed three times with serum-free media, and then incubated with 2 μM of the compound of Formula 7 in serum-free media for 20 min at 37° C. The cells were washed three times with phosphate buffered saline (PBS; Gibco) and then imaged after further incubation in colorless serum-free media for 15 min.

The pseudo colored TPM images of cultured astrocytes labeled with the compound (2 μM) of Formula 7 showed intense spots and homogeneous domains (FIG. 12). It has been estimated that the image was attributed to the TPEF emitted from the intracellular Ca$^{2+}$ complex with the compound of Formula 4 and membrane-bound probes because the fluorescence quantum yields of the compound of Formula 4-Ca$^{2+}$ in MOPS buffer (0.49) and the compound of Formula 7 in DMF (0.27) are much higher than those of the compound of Formula 4 (0.012) and the compound of Formula 7 (0.060) in MOPS buffer (Table 2), and the compound of Formula 7 in DM F has been assumed to be a good model for the membrane-bound probes due to the similarity in $\lambda_{max}^{fl}$.

The TPEF spectra of the intense spots and homogeneous domains showed emission maxima at 445 (FIG. 12b, blue curve) and 494 nm (FIG. 12b, red curve), respectively. Moreover, the blue emission band was asymmetrical and could be fitted to two Gaussian functions with emission maxima at 445 and 488 nm (FIG. 12b, sky blue curves), respectively, whereas the red emission band could be fitted to a single Gaussian function with maximum at 500 nm (FIG. 12b, brown curve). Compared with the emission spectra recorded in MOPS buffer (FIG. 2a), the shorter wavelength band of the dissected spectrum was significantly blue shifted while the longer wavelength to band remained similar. The spectral shift suggests that the probes may be located in two regions of differing polarity.

To assess the polarity of environments, lifetime images of astrocytes labeled with the compound of Formula 7 were obtained.

Astrocytes were grown on coverslip in 10% FBS containing DMEM. Cells were washed briefly in PBS and incubated with 2 μM of the compound of Formula 7 for 20 min at 37° C. Cells were washed with PBS three times, fixed with formaldehyde (3.7% in PBS) for 10 min, washed with PBS three times and then mounted with mounting solution. The fluorescence decays were resolved by time-correlated single-photon counting (TCSPC) using an SPC830 acquisition board (Becker & Hickl, Berlin) synchronized with a Leica TSC-SP2-AOBS confocal microscope. The results are shown in FIGS. 13a to 13d.

Referring to these figures, the intense spot exhibited an excited state lifetime of 1.8 ns, more than 2-fold longer than the upper extreme of the lifetime distribution curve centered at ~0.8 ns. This result may reflect two distinct environments populated by the probe of the present invention, a hydrophilic one that is likely to be cytosolic, which emits red light with a shorter lifetime, and a hydrophobic one, likely to be membrane-associated, with longer-lived blue emission.

The intracellular Ca$^{2+}$ could be detected with minimum errors due to the membrane-bound probes. The spectrum of the shorter wavelength band in the dissected Gaussian function (FIG. 12b, sky blue curve) decreased to baseline at ~500 nm, indicating that the TPEF emitted from the membrane-bound probes contributes negligible interference at $\lambda$>500 nm. Similarly, if it is considered that the compound of Formula 7 in DMF is as a model for membrane-bound probe, the fluorescence at $\lambda$>500 nm accounts for only 5% of the total emission band (FIG. 1b). Consistently, the TPEF image collected at 500-620 nm is homogeneous without the intense spots (FIG. 14b), whereas that collected at 360-460 nm clearly shows them (FIG. 14a). Therefore, the intracellular Ca$^{2+}$ can be selectively detected by using the detection window at 500-620 nm.

To demonstrate the utility of this probe, [Ca$^{2+}$]$_i$ waves in live cells and tissue were monitored. The TPM images of cultured astrocytes labeled with the compound (2 μM) of Formula 7 revealed the spontaneous Ca$^{2+}$ signal propagation from the astrocytic process (1) to soma (2) to terminal (3) with a speed of 7.5±2.2 μm/s (n=5 astrocytes) (FIGS. 15a and 15c). The spontaneous increase in [Ca$^{2+}$]$_i$ also propagated between astrocytes, as indicated by the delayed activity in the neighboring astrocyte (FIGS. 15b and 15d).

The speed of propagation of spontaneously occurring waves was 1.8±1.1 μm/s (n=7 astrocytes), a result consistent with reported data (H. R. Parri, T. M. Gould, V. Crunelli, *Nat. Neurosci.* 2001, 4, 803-812). Thus, the compound of Formula 4 is clearly capable of visualizing the intra- and intercellular calcium waves in cultured astrocytes using TPM.

Example 5

Observations of Acute Rat Hypothalamic Slices

Slices were prepared from the hippocampi and the hypothalmic of 2-day-old rat (SD). Coronal slices were cut into 400 μm thick using a vibrating-blade microtome in artificial cerebrospinal fluid (ACSF; 138.6 mM NaCl, 3.5 mM KCl, 21 mM NaHCO$_3$, 0.6 mM NaH$_2$PO$_4$, 9.9 mM D-glucose, 1 mM CaCl$_2$, and 3 mM MgCl$_2$). Slices were incubated with the compound (10 μM) of Formula 7 in ACSF bubbled with 95% O$_2$ and 5% CO$_2$ for 30 min at 37° C. Slices were then washed three times with ACSF and transferred to glass-bottomed dishes (MatTek) and observed in a spectral confocal multi photon microscope.

To obtain the TPM images of the CA1 region in the presence of 20 μM N,N,N',N'-terakis(2-pyridyl)ethylenediamine (TPEN), a membrane permeable Zn$^{2+}$ chelator that can effectively remove Zn$^{2+}$ by chelation without causing toxic effect (C. M. Matias, N.C. Matos, M. Arif, J. C. Dionisio, M. E. Quinta-Ferreira, *Biol. Res.* 2006, 39, 521-530), a 20 mM stock solution of TPEN was prepared by dissolving 8.5 mg of TPEN in 1.0 mL of ethanol (M. E. Quinta-Ferreira, C. M. Matias, *Brain Res.* 2004, 1004, 52-60). A 1.0 μl of this solution was added to 1.0 mL of ACSF to prepare 20 μM TPEN in ACSF. After taking the TPM image of the hippocampal slice labeled with the compound of Formula 7, the ACSF solution in the glass-bottomed dish was removed with a micropipette, 1 mL of 20 μM TPEN in ACSF was added, and then TPM image was obtained.

FIG. 16 shows pseudo colored TPM images of an acute rat hypothalamic slice stained with the compound (10 μM) of Formula 7 taken after 195 s (16a) and 214 s (16b), and FIG. 17 shows spontaneous Ca$^{2+}$ transients recorded in soma (1), astrocyte process (2), and neighboring cell (3) in FIG. 16.

Referring to FIG. 17, the spontaneous Ca$^{2+}$ waves in the soma could be clearly visualized with a frequency of about 16 mHz (n=4 slices) for more than 1100 s without appreciable decay. Furthermore, the spikes at the astrocyte process appeared slightly before those in the soma, confirming the previous finding that the signals propagate progressively from the process to the soma (J. Y. Koh, S. W. Suh, B. J. Gwag, Y. Y. He, C. Y. Hsu, D. W. Choi, *Science* 1996, 272, 1013-1016).

Similar results were reported for TTX treated thalamus slices stained with fura-2 (H. R. Parri, T. M. Gould, V. Crunelli, *Nat. Neurosci.* 2001, 4, 803-812), except that the image revealed damaged cells on the tissue surface and was not as clear as the TPM image presented in the present invention. Also, the TTX fluorescence intensity decayed appreciably after 500 s.

The improved TPM image of tissue labeled with the compound of Formula 4 obtained at ~170 μm depth for a prolonged observation time underlines the high photo-stability and low photo-toxicity of the probe according to the present invention in addition to the capability of deep tissue imaging.

Finally, the spikes at the process became very weak after 700 s, probably because it has moved away from the focal point under the microscope. As can be seen from the data in FIG. 17, a similar calcium wave was also observed in a different cell.

The invention claimed is:

1. A two-photon probe for real-time monitoring of intracellular calcium ions, said probe being represented by Formula 1:

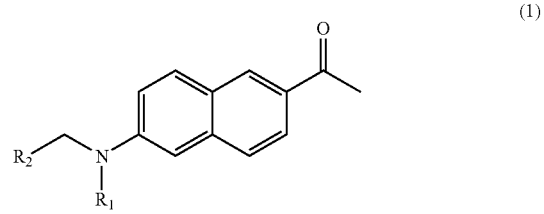

wherein R$_1$ is CH$_3$ or H,
R$_2$ is

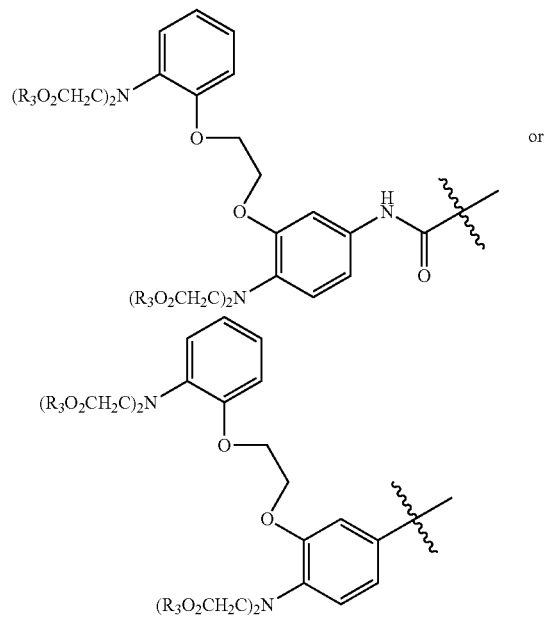

and R$_3$ is H or CH$_2$OCOCH$_3$.

2. The two-photon probe according to claim 1, wherein R$_3$ is CH$_2$OCOCH$_3$.

3. A method for preparing a two-photon probe for real-time monitoring of intracellular calcium ions, said probe being represented by Formula 1:

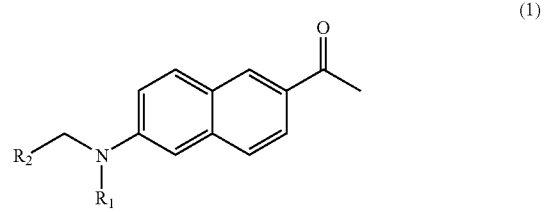

wherein $R_1$ is $CH_3$ or H, and $R_2$ is

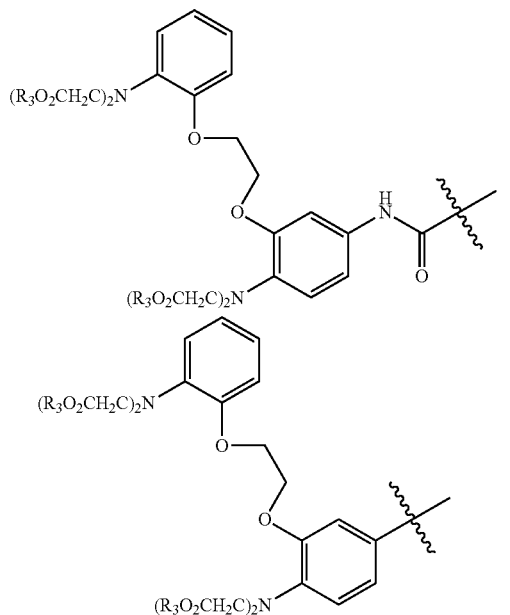

and $R_3$ is H or $CH_2OCOCH_3$,
the method comprising reacting a compound of Formula 2:

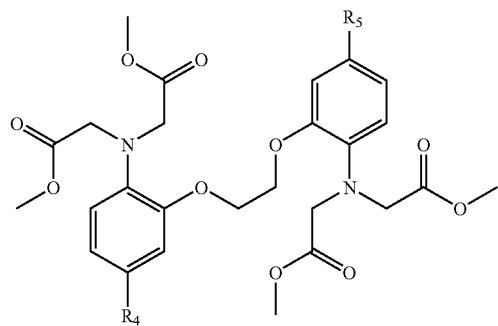

wherein $R_4$ is $NH_2$ or CHO and $R_5$ is H or $CH_3$, with a compound of Formula 3:

wherein $R_6$ is $NH_2$ or

4. The method according to claim 3, wherein the hydrogen atoms in $R_3$ are replaced with $CH_2OCOCH_3$ by reacting bromomethyl acetate and triethylamine with the compound of Formula 1 ($R_3$=H).

5. A method for real-time monitoring of intracellular calcium ions, the method comprising introducing the two-photon probe according to claim 1 into cells of interest and imaging two-photon excited fluorescence emitted from the two-photon probe.

6. The method according to claim 5, comprising quantitatively determining intracellular calcium ion concentration using Equation 1:

$$[Ca^{2+}] = K_d[(F-F_{min})/(F_{max}-F)] \quad (1)$$

where $K_d$ is the dissociation constant of the two-photon probe for $Ca^{2+}$, F is the observed two-photon fluorescence intensity, $F_{min}$ is the minimum fluorescence intensity, and $F_{max}$ is the maximum fluorescence intensity.

7. The method according to claim 5, wherein the two-photon excited fluorescence imaging is at wavelengths ranging from 500 to 620 nm.

* * * * *

UNITED STATES PATENT AND TRADEMARK OFFICE
CERTIFICATE OF CORRECTION

PATENT NO.        : 8,084,647 B2
APPLICATION NO.   : 11/997520
DATED             : December 27, 2011
INVENTOR(S)       : Cho et al.

It is certified that error appears in the above-identified patent and that said Letters Patent is hereby corrected as shown below:

Column 3,
Line 2, "Formula" should read --Formula 3--.

Column 9,
Line 61, Equation 3 should read:
--$[LM]^2 - ([L]_0+[M]_0+K_d)[LM]+[L]_0[M]_0=0$--.

Column 11,
TABLE 2 should read:

| Compound[a] | $\lambda_{max}^{(1)}$ [b] | $\lambda_{max}^{fl}$ [b] | $\Phi$ [c] | $K^{OP}/K^{TP}$ [d] | $FEF^{OP}/FEF^{TP}$ [e] | $\lambda_{max}^{(2)}$ [f] | $\delta$ [g] | $\Phi\delta$ [h] |
|---|---|---|---|---|---|---|---|---|
| Formula 7 | 362 | 495 | 0.060[f] | | | nd[i] | nd[i] | nd[i] |
| Formula 4 | 365 | 498 | 0.012 | | | nd[i] | nd[i] | nd[i] |
| Formula 4-Ca$^{2+}$ | 365 | 498 | 0.49 | 0.27[k]/0.25 | 40/44 | 780 | 230 | 110 |
| OG1+Ca$^{2+}$ | 494 | 523 | 0.66 | 0.17[i]/nd | 14[i]/nd | 800 | 37 | 24 |

Signed and Sealed this
Seventeenth Day of July, 2012

David J. Kappos
*Director of the United States Patent and Trademark Office*